United States Patent [19]

Eason

[11] Patent Number: 5,220,094
[45] Date of Patent: Jun. 15, 1993

[54] ALKYLATION RECONTRACTOR WITH INTERNAL MIXER

[75] Inventor: John H. Eason, Katy, Tex.

[73] Assignee: Phillips Petroleum Company, Bartlesville, Okla.

[21] Appl. No.: 855,976

[22] Filed: Mar. 23, 1992

[51] Int. Cl.$^5$ .................................................. C07C 2/62
[52] U.S. Cl. ................................... 585/716; 585/719; 585/720; 585/723
[58] Field of Search ............... 585/716, 719, 720, 723

[56] References Cited

U.S. PATENT DOCUMENTS

| | | |
|---|---|---|
| 3,080,438 | 3/1963 | Sailors ............................ 260/683.48 |
| 3,911,043 | 10/1975 | Anderson ............................ 585/716 |
| 3,919,342 | 11/1975 | Chapman ....................... 260/683.42 |
| 3,925,501 | 12/1975 | Putney et al. ........................ 585/723 |
| 4,046,516 | 9/1977 | Burton et al. ........................ 585/716 |
| 4,161,497 | 7/1979 | Mkkover et al. .................... 585/719 |
| 4,162,273 | 7/1979 | Skraba ................................. 585/854 |
| 4,249,030 | 2/1981 | Chapman et al. ................... 585/723 |
| 4,371,731 | 2/1983 | Washer ................................ 585/716 |
| 4,579,998 | 4/1986 | Hutson, Jr. .......................... 585/716 |

*Primary Examiner*—Anthony McFarlane
*Attorney, Agent, or Firm*—Ryan N. Cross

[57] ABSTRACT

An improved alkylation recontactor is provided, wherein the recontactor utilizes an internal mixer for mixing hydrocarbon effluent from an alkylation zone with an acid catalyst from an acid inventory vessel in fluid flow communication with the interior of the recontactor.

6 Claims, 2 Drawing Sheets

ALKYLATION RECONTRACTOR WITH INTERNAL MIXER

In one aspect, the invention relates to a method of recontacting an alkylation effluent with an acid catalyst wherein the effluent and acid are mixed within the recontactor. In another aspect the invention relates to an apparatus for recontacting an alkylation effluent with an acid catalyst wherein the mixer for the recontactor is inside the recontactor.

One of the major problems associated with catalytic alkylation of hydrocarbons lies in handling the alkylation catalyst, that is, transporting the catalyst through the various parts of the reaction and recovery system. The problem is particularly aggravated when an acid catalyst, such as hydroflouric acid (HF), sulfuric acid, etc., is used since these materials in many instances are highly corrosive to ordinary materials of construction. Special equipment such as alloy valves, special pumps, and pump packings are required and special safety precautions are necessary in the alkylation of hydrocarbons with an acid catalyst. It is therefore economically desirable to eliminate expensive valves and flanges. Furthermore, it is desirable from a safety and environmental standpoint to eliminate valves and flanges which might leak to the atmosphere or confine them so that any leaks will have no direct atmospheric contact.

Accordingly, an object of this invention is to provide an improved apparatus and process for carrying out contacting in an alkylation process that eliminates expensive valves and flanges.

Another object of this invention is to provide an improved alkylation process and apparatus for carrying out contacting in an alkylation process wherein valves and flanges which can leak to the atmosphere are eliminated or confined so that any leak has no direct atmospheric contact.

Still another object of this invention is to improve the safety of an alkylation process and apparatus.

Yet another object of this invention is to increase the economy of an alkylation process and apparatus.

In accordance with the present invention, there is provided a process for recontacting a hydrocarbon effluent from an alkylation zone with an acid catalyst in an alkylation process comprising: withdrawing the hydrocarbon effluent from said alkylation zone; transferring the hydrocarbon effluent to a mixing zone located within a recontacting zone; transferring the acid catalyst from an acid inventory zone located within the recontacting zone to the mixing zone; mixing the acid catalyst and the hydrocarbon effluent in the mixing zone to form an acid-effluent mixture; flowing the acid-effluent mixture into a settling zone contained within the recontacting zone; settling at least part of the acid catalyst in said acid-effluent mixture to the acid inventory zone from the settling zone; and withdrawing the remaining acid-effluent mixture from the recontacting zone.

According to another aspect of the invention, there is provided an apparatus for the alkylation of an isoparaffin with an olefin in the presence of an acid catalyst comprising: contacting means for contacting the isoparaffin, the olefin and the acid catalyst to produce a contacting effluent comprising hydrocarbons and said acid catalyst; settling means in fluid flow communication with the contacting means for receiving said contacting effluent and at least partially separating the acid catalyst from the hydrocarbons to produce said thus separated acid catalyst and a hydrocarbon effluent; and a recontactor in fluid flow communication with the settling means for receiving the hydrocarbon effluent from the settling means, the recontactor comprising a recontactor settling vessel, an acid inventory vessel in fluid flow communication with the recontactor settling vessel for containing an additional acid catalyst, mixing means inside the recontactor for mixing the hydrocarbon effluent with the acid catalyst from the acid inventory vessel to produce an acid-effluent mixture, means in fluid flow communication between the mixing means and the acid inventory vessel for conveying the acid catalyst from the acid inventory vessel to the mixing means, means operatively related to said mixing means for passing the acid-effluent mixture from said mixing means to the recontactor settling vessel wherein at least part of the acid catalyst in the acid-effluent mixture can settle into the acid inventory leaving a recontactor effluent there above, and means in fluid flow communication with said recontactor settling vessel for removing the recontactor effluent from the recontactor settling vessel.

According to yet another aspect of the invention, there is provided an apparatus suitable for recontacting a hydrocarbon effluent from an alkylation zone with an acid catalyst comprising: a recontactor comprising a settling vessel; an acid inventory vessel located below the settling vessel and in a fluid flow communication with the settling vessel, wherein the acid inventory vessel is adapted to contain a quantity of the acid catalyst; mixing means located in the settling vessel for receiving hydrocarbon effluent from the alkylation zone and acid catalyst from the acid inventory vessel, for mixing hydrocarbon effluent and acid catalyst to form an acid-effluent mixture, and for releasing said acid-effluent mixture to the settling vessel; and means for conveying acid catalyst from the acid inventory vessel to the mixing means.

A better understanding of the invention will be obtained upon reference to the accompanying drawings of which:

Figure 1:
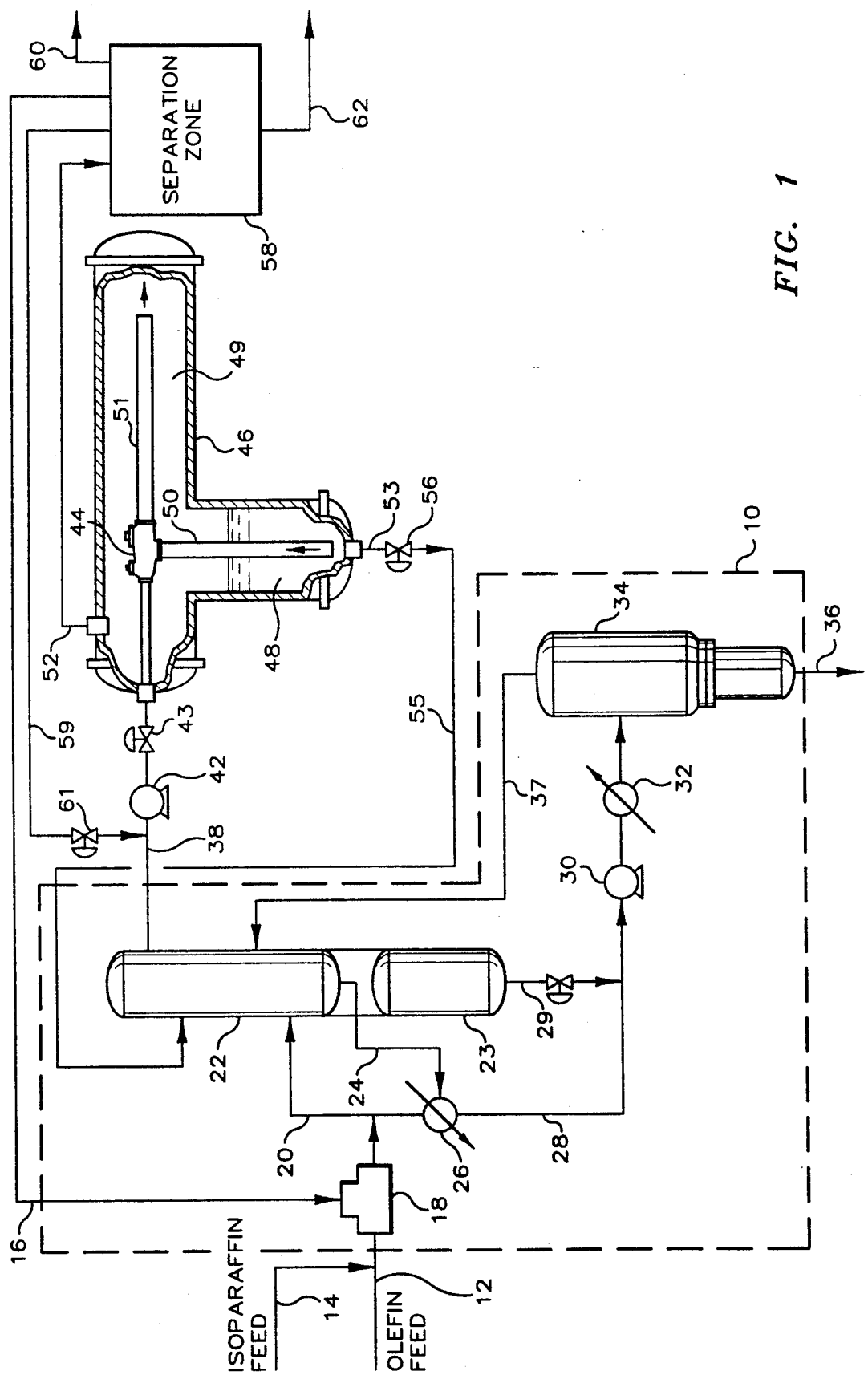
FIG. 1 is a diagrammatic illustration of an alkylation process utilizing the present invention with the mixer inside the recontactor.

Referring now to FIG. 1, the alkylation unit diagrammatically illustrated includes HF alkylation zone 10, recontactor 46 and a separation zone 58. HF alkylation zone 10 includes reactor 20, and phase separator or settler 22.

Olefin feed, isoparaffin feed, and recycle isoparaffin are charged to alkylation zone 10 via conduits 12, 14 and 16, respectively, where they enter feed-recycle mixer 18. The isoparaffin-olefin feed is contacted with an acid catalyst in a contacting means or reaction zone, such as reactor pipe 20. From reactor pipe 20 the contacting effluent, which can contain hydrocarbon product (alkylate), acid catalyst, alkyl fluorides and other hydrocarbons, is introduced to settler 22. Acid catalyst is removed from the bottom of settler 22 and flows through conduit 24 to heat exchanger 26 where it is cooled and split. Part of the acid catalyst returns to reactor pipe 20 and the rest is pumped through conduit 28 by pump 30, heated in heat exchanger 32 and then introduced to acid rerun vessel 34. The bottoms of acid rerun vessel 34 are removed through conduit 36 and treated to produce acid soluble oil (ASO) product. The acid catalyst is removed from the top of acid rerun vessel 34 and introduced into settler 22 via conduit 37 which is in fluid flow communication with acid rerun vessel 34 and settler 22. Additionally, makeup acid catalyst can be introduced from acid storage 23 into conduit 28 via conduit 29 when needed.

Hydrocarbon effluent is removed from the alkylation zone 10 via conduit 38, the hydrocarbon effluent being pumped through conduit 38 and valve 43 by pump 42 into internal mixer, shown as internal eductor 44, disposed entirely within a recontacting zone shown as recontactor 46. The flow of effluent into internal eductor 44 is controlled by valve 43. Recontactor 46 comprises settling vessel or settling zone 49 and acid inventory zone 48. Acid is drawn from acid inventory 48 into internal eductor 44 via conduit 50, which provides fluid flow communication between acid inventory 48 and internal eductor 44. Internal mixing line 51 has an inlet end in fluid flow communication with mixer 44 and an outlet end in fluid flow communication with the interior of settling vessel 49. Internal eductor 44 and mixing line 51 form a mixing zone, where hydrocarbon effluent is mixed with acid catalyst received from below from acid inventory 48 of recontactor 46 to produce an acid-effluent mixture. The acid-effluent mixture enters internal mixing line 51 from eductor 44 and flows from mixing line 51 into settling vessel 49. Additionally in the mixing zone and settling vessel 49 the alkylate is purified of at least part of its impurities. For example, in the case of a hydrofluoric acid (HF) catalyst the alkylate is purified of alkyl fluorides. In recontactor 46 separation occurs so that at least part of the acid catalyst in the acid-effluent mixture settles by means of gravity from settling vessel or zone 49 into acid inventory 48. The remaining acid-effluent mixture, containing alkylate and isobutane is removed from recontactor 46 through conduit 52 as recontactor effluent. Typically, recontactor 46 will be run, so that it is full of liquid; thus, the recontactor effluent can be readily removed from the gravitational top of recontactor 46.

Conduit 52 is in fluid flow communication with both recontactor 46 and separation zone 58. Recontactor effluent entering separation zone 58 through conduit 52 is separated into products, including $C_3$ and lighter products removed through conduit 60 and alkylate and n-butane products removed through conduit 62. Isoparaffin is removed from the alkylate and is recycled and returned in alkylation zone 10 via conduit 16 where it is introduced to the feed stream and feed-recycle mixer 18. Acid catalyst removed from the alkylate in separation zone 58 flows into conduit 38 via conduit 59 and is returned to the recontactor via conduit 38. Flow into conduit 38 is controlled by valve 61.

Acid and alkylate impurities from acid inventory 48 are removed by conduit 53 into conduit 55 which is in fluid flow communication with settler 22. Flow through conduits 53 and 55 is controlled by valve 56. The amount of acid in the acid inventory can be controlled by an automated level controller (not shown) which adjusts valves 56 and 61 to maintain a suitable acid level.

The present invention, as illustrated in FIG. 1, and the above description eliminates several valves and their associated flanges from conventional alkylation units, thus reducing sites where leaks to the atmosphere can possibly take place and decreasing expense by elimination of costly valves. Also, the use of an internal mixer and internal mixing line within the recontactor vessel 46 eliminates sites where leaks to the atmosphere can occur by placing them within the recontactor and eliminates a low point in the conventional recontacting process which can be difficult to drain safely for maintenace. The low point referred to in prior alkylation units is created by the connection between the lowest part of the prior acid inventory and the eductor positioned external and below to the prior acid inventory vessel. Additionally, the use of an internal mixer located above the acid inventory vessel in accordance with the present invention, as opposed to in the acid inventory vessel, reduces the size of the acid inventory vessel needed and, therefore, reduces the risk of leaks in the acid inventory vessel thereby improving the safety of operation of an alkylation process which employes the present invention. Therefore, it can be seen that the present invention has several advantages from a safety and environmental standpoint.

Figure 2:
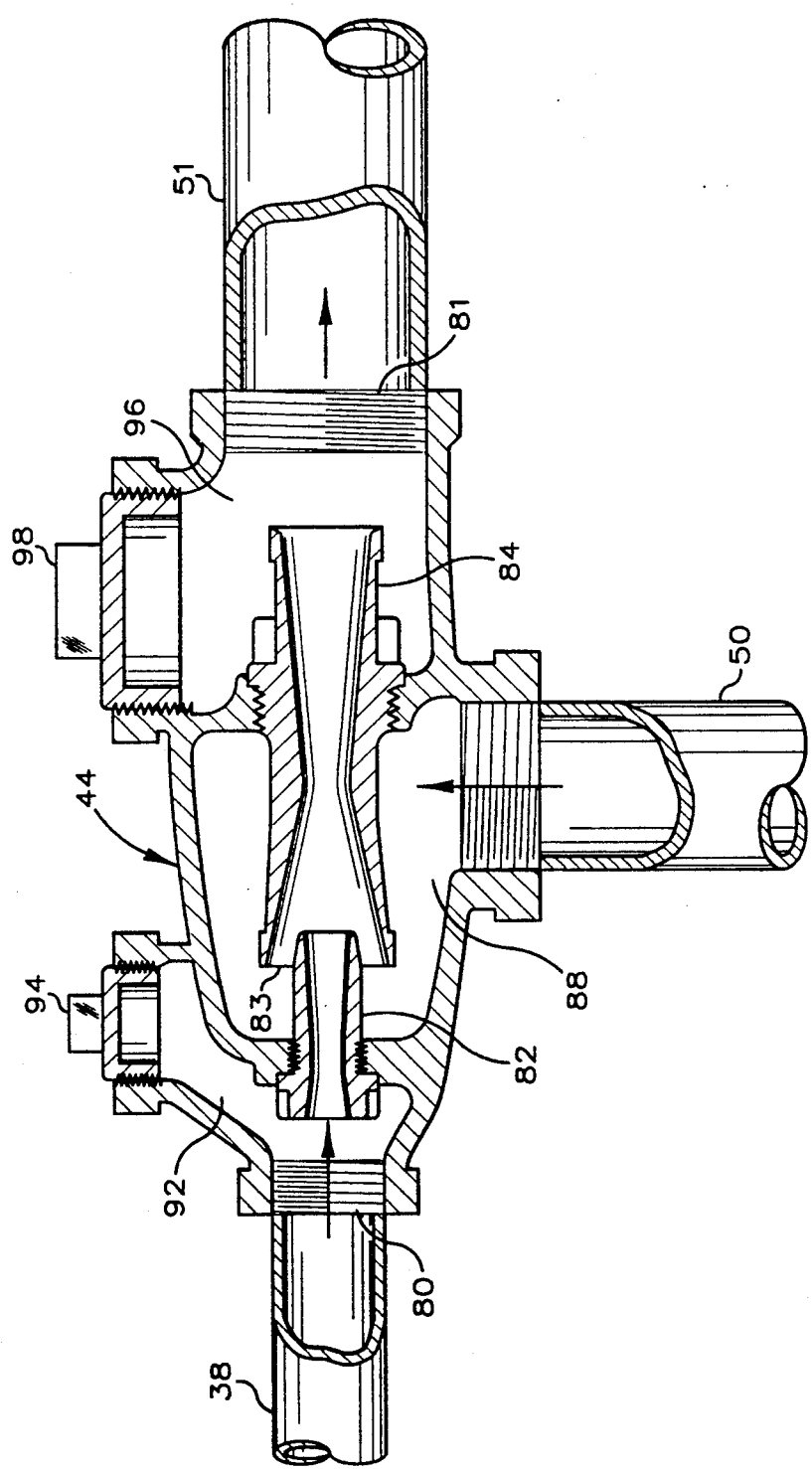
FIG. 2 is an isometric illustration of eductor-type mixer suitable for use in the present invention.

Referring now to FIG. 2, a mixer of the eductor type is shown which is suitable for use in the present invention. Eductor 44 has two nozzles, a first nozzle 82 and venturi nozzle 84. The nozzles are arranged such that first nozzle 82 is in fluid flow communication with conduit 38, and venturi nozzle 84 is in fluid flow communication with first nozzle 82 and conduit 51. Additionally, eductor 44 has suction chamber 88 which is in fluid flow communication with venturi nozzle 84, through venturi nozzle channel 83, and with conduit 50. As shown, eductor 44 has a first channel 92 and a second channel 96 which have a first channel cap 94 and a second channel cap 98, respectively.

Hydrocarbon effluent enters eductor 44 via conduit 38 which is attached to eductor 44 by means of coupling 80. The incoming hydrocarbon effluent flows from conduit 38 into first nozzle 82 and then from first nozzle 82 into venturi nozzle 84. First nozzle 82 and venturi nozzle 84 are designed so that hydrocarbon effluent from conduit 38 undergoes pressure and velocity changes in the two nozzles sufficient to develop a pressure at venturi nozzle channel 83 that is lower than the pressure in suction chamber 88. Therefore, a suction develops that causes some of the acid in suction chamber 88 to be entrained with the hydrocarbon effluent in venturi nozzle 84. Subsequently, the suction of fluid out of suction chamber 88 causes acid to be drawn into suction chamber 88 from conduit 50 and, similarly, acid is drawn from the acid inventory into conduit 50.

The acid-effluent mixture, produced by the entrainment of the acid with the effluent, flows from venturi nozzle 84 into conduit 51, which is attached to eductor 44 by means of coupling 81.

Because the acid inventory is below the mixer in the above-described invention, it is necessary to have a means to move the acid from the acid inventory to the mixer, such as a pump or aspirator. The mixer of FIG. 2 is in the form of an eductor and takes advantage of aspiration to both move the acid from the acid inventory to the eductor and thereafter combine the acid with the hydrocarbon effluent.

Although the invention as detailed above is new, general process parameters as detailed in U.S. Pat. Nos. 3,080,438 and 3,919,342, the disclosures of which are hereby incorporated by reference, are applicable to the present invention.

Generally, the total amount of hydrocarbon contacted with the acid catalyst introduced into the mixing zone of the recontactor should be sufficient to maintain the hydrocarbon as a continuous phase. Generally, the amount of acid in the mixing zone will be less than about 50 volume percent, and above about 25 volume percent.

In general, any of the conventional catalytic alkylation reactions can be carried out by the process of the present invention. Thus, the alkylation reaction can comprise reaction of an isoparaffin with an olefin, or reaction of an aromatic hydrocarbon with an olefin or other alkylating agent, the reaction in each instance being carried out in the presence of a suitable alkylation catalyst. In place of an olefin as an alkylating agent, various alcohols and ethers, such as isopropyl alcohol, tert-butyl alcohol, secondary butyl alcohol, isopropyl ether, and the like, can be carried out in the presence of a suitable alkylation catalyst. Likewise, the alkyl halides, sulfates and phosphates of the olefins can be used as the alkylation agent with an appropriate or compatible alkylation catalyst.

The alkylation reaction is carried out with the hydrocarbon reactants in a liquid phase; however, the reactants need not be normally liquid hydrocarbons. The reaction condition can vary in temperature from sub-zero temperatures to temperatures as high as 200° F., and can be carried out at pressures varying from atmospheric to as high as 1000 psi, and higher. A variety of alkylation catalysts can be employed in the alkylation reaction, including the well known catalysts, such as sulfuric acid, hydrofluoric acid (HF), phosphoric acid, metal halides, such as aluminum chloride, bromide, etc., or other liquid alkylation catalysts; however, hydrofluoric acid is preferred.

While generally applicable to the alkylation of hydrocarbons, the present invention is particularly effective for alkylation using low boiling olefins such as propylene, butenes, pentenes, etc., and saturated branched chained paraffins, such as isobutane, in the presence of hydrofluoric acid. In the alkylation of isoparaffins with olefins in the presence of HF, a substantial molar excess of isoparaffin over olefin is employed, generally to provide an external feed ratio in excess of 1:1, usually from about 4:1 to about 20:1, and preferably from 5:1 to 15:1. The reaction zone is maintained under sufficient pressure to insure that the hydrocarbon reactants and alkylation catalysts are in the liquid phase. The temperature of the reaction will vary with the reactants and with the catalysts employed, but generally ranges from about $-40°$ F. to about 150° F., preferably from 70° F. to 120° F.

From the above description and figures, it can be seen that the present invention improves the safety and economy of alkylation processes.

Various modifications and alteration of this invention will become apparent to those skilled in the art without departing from the scope and spirit of this invention, and it should be understood that the foregoing discussion and figures are merely set forth for illustrative purposes and should not unduly limit this invention.

That which is claimed is:

1. A process for contacting a hydrocarbon effluent from an alkylation zone with an acid catalyst in an alkylation process, wherein said contacting occurs in a contacting vessel containing a settling zone, an acid inventory zone, and a mixing zone, comprising:
   (a) withdrawing said hydrocarbon effluent from said alkylation zone;
   (b) transferring said hydrocarbon effluent to said mixing zone;
   (c) transferring said acid catalyst from said acid inventory zone to said mixing zone;
   (d) mixing said acid catalyst and said hydrocarbon effluent in said mixing zone to form an acid-effluent mixture;
   (e) flowing said acid-effluent mixture into a settling zone;
   (f) settling at least part of said acid catalyst in said acid-effluent mixture to said acid inventory zone from said settling zone to leave a remaining acid-effluent mixture in said settling zone; and
   (g) withdrawing said remaining acid-effluent mixture from said contacting vessel.

2. A process according to claim 1 wherein said acid catalyst is HF acid catalyst.

3. A process according to claim 1 wherein said mixing zone and said settling zone are above said acid inventory zone and said mixing zone is located within said settling zone.

4. A process according to claim 1 further comprising after said step (d), and before said step (e), flowing said acid-effluent mixture through a mixing line having an inlet end and an outlet end, said inlet end being located at said mixing zone and said outlet end being located at said settling zone.

5. A process according to claim 4 wherein said step (g) is performed at an opposite end of said settling zone from said outlet end of said mixing line.

6. A process according to claim 5 wherein said mixing zone and said settling zone are above said acid inventory zone, said mixing zone is located within said settling zone and said acid catalyst is HF acid catalyst.

* * * * *